(12) United States Patent
Kück et al.

(10) Patent No.: US 7,074,196 B2
(45) Date of Patent: Jul. 11, 2006

(54) ALGORITHMS, SYSTEMS, AND METHODS FOR ESTIMATING CARBON DIOXIDE STORES, TRANSFORMING RESPIRATORY GAS MEASUREMENTS, AND OBTAINING ACCURATE NONINVASIVE PULMONARY CAPILLARY BLOOD FLOW AND CARDIAC OUTPUT MEASUREMENTS

(75) Inventors: Kai Kück, Hamburg (DE); Joseph A. Orr, Park City, UT (US); Lara Brewer, Bountiful, UT (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 11/102,072

(22) Filed: Apr. 8, 2005

(65) Prior Publication Data

US 2005/0177055 A1 Aug. 11, 2005

Related U.S. Application Data

(63) Continuation of application No. 10/121,219, filed on Apr. 11, 2002, now Pat. No. 6,955,651, which is a continuation-in-part of application No. 06/510,702, filed on Feb. 22, 2000, now Pat. No. 6,540,689.

(51) Int. Cl.
*A61B 5/00* (2006.01)
(52) U.S. Cl. .......................... 600/532; 73/23.3; 422/84
(58) Field of Classification Search ................. 600/532; 73/23.3; 422/84
See application file for complete search history.

(56) References Cited

U.S. PATENT DOCUMENTS

| | | | |
|---|---|---|---|
| 4,221,224 A | 9/1980 | Clark | |
| 4,463,764 A | 8/1984 | Anderson et al. | |
| 5,060,656 A | 10/1991 | Howard | |
| 5,069,220 A | 12/1991 | Casparie et al. | |
| 5,117,674 A | 6/1992 | Howard | |
| 5,178,155 A | 1/1993 | Mault | |
| 5,285,782 A | 2/1994 | Prosser | |
| 5,285,794 A | 2/1994 | Lynch | |
| 5,299,579 A | 4/1994 | Gedeon et al. | |
| 5,402,796 A | 4/1995 | Packer et al. | |

(Continued)

FOREIGN PATENT DOCUMENTS

DE 28 49 217 A1 5/1980

(Continued)

OTHER PUBLICATIONS

H. Blomquist et al., *A Non-Invasive Technique for Measurement of Lung Perfusion*, Intensive Care Medicine 1986; 12:172.

(Continued)

*Primary Examiner*—Robert L. Nasser
(74) *Attorney, Agent, or Firm*—TraskBritt

(57) ABSTRACT

Methods for estimating the volume of the carbon dioxide stores of an individual's respiratory tract include determining a carbon dioxide store volume at which a correlation between corresponding signals of carbon dioxide elimination and an indicator of the content of carbon dioxide in blood of the individual is optimized. The estimate of the volume of carbon dioxide stores, which comprises a model of the respiratory tract, or lungs, of the individual, may be used as a transformation to improve the accuracy of one or both of the carbon dioxide elimination and carbon dioxide content signals. Transformation, or filtering, algorithms are also disclosed, as are systems in which the methods and algorithms may be used. The methods, algorithms, and systems may be used to accurately and noninvasively determine one or both of the pulmonary capillary blood flow and cardiac output of the individual.

42 Claims, 8 Drawing Sheets

U.S. PATENT DOCUMENTS

| | | | |
|---|---|---|---|
| 5,632,281 | A | 5/1997 | Rayburn |
| 5,836,300 | A | 11/1998 | Mault |
| 5,971,934 | A | 10/1999 | Scherer et al. |
| 6,059,732 | A | 5/2000 | Orr et al. |
| 6,102,868 | A | 8/2000 | Banner et al. |
| 6,135,107 | A | 10/2000 | Mault |
| 6,200,271 | B1 | 3/2001 | Kuck et al. |
| 6,210,342 | B1 | 4/2001 | Kuck et al. |
| 6,217,524 | B1 | 4/2001 | Orr et al. |
| 6,227,196 | B1 | 5/2001 | Jaffe et al. |
| 6,238,351 | B1 | 5/2001 | Orr et al. |
| 6,306,098 | B1 | 10/2001 | Orr et al. |
| 6,394,962 | B1 | 5/2002 | Gama De Abreu et al. |
| 6,402,697 | B1 | 6/2002 | Calkins et al. |
| 6,540,689 | B1 | 4/2003 | Orr et al. |
| 2002/0169365 | A1* | 11/2002 | Heinonen et al. ........... 600/531 |

FOREIGN PATENT DOCUMENTS

| | | |
|---|---|---|
| WO | WO 96/12963 | 4/1996 |
| WO | WO 96/24285 | 8/1996 |

OTHER PUBLICATIONS

R.J. Bosman et al, *Non-Invasive Pulimonary Blood Flow Measurement by Means of $CO_2$ Analysis Of Expiratory Gases*, Intensive Care Medicine 1991, 17:98-102.

A. Gedeon, *Non-Invasive Pulmonary Blood Flow for Optimal Peep*, ICOR AB, Ulvsundavagen 178 B, S-161 30 Bromma, Sweden, pp. 49-58.

Capek, J.M., *Noninvasive Measurement of Cardiac Output Using Partial $CO_2$ Rebreathing* [Dissertation], Rensselaer Polytechnic Institute (1988) 28:351 p. (due to large number of pages, only table of contents and abstract have been copied).

Capek, J.M., et al., *Noninvasive Measurement of Cardiac Output Using Partial $CO_2$ Rebreathing*, IEEE Trans. Biomed. Eng. (1988) 35(9):653-61.

Davies, Gerald G., et al., *Continuous Fick cardiac output compared to thermodilution cardiac output*, Critical Care Medicine (1986) 14(10):881-85.

Elliot, C. Gregory, et al., *Complications of Pulmonary Artery Catheterization in the Care of Critically Ill Patients*, Chest (1979) 76:547-52.

Fick, A., *Über die Messung des Blutquantums in den Herzventrikeln*, Sitzungsbericht der Physikalisch-Medizinischen Gesellschalt zu Würzburg (1870) 36 (2 pages).

Gama de Abreu, Marcelo, et al., *Measurement of Pulmonary Capillary Blood Flow for Trending Mixed Venous Blood Oxygen Saturation and Oxygen Delivery*, Crit. Care Med. (1998), vol. 26, No. 1 (Suppl.), A106, Abstract #238, (1 page).

Gama de Abreu, Marcelo, et al., *Is the Partial $CO_2$ Rebreathing Technique a Useful Tool for Trending Pulmonary Capillary Blood Flow During Adjustments of Peep?*, Crit. Care Med. (1998), vol. 26, No. 1 (Suppl.), A106, Abstract #237, (1 page).

Gama de Abreu, et al., *Partial carbon dioxide rebreathing: A reliable technique for noninvasive measurement of nonshunted pulmonary capillary blood flow*, Crit. Care Med. (1997) 25(4):675-83.

Gedeon, A., et al., *Noninvasive Cardiac Output Determined with a New Method Based on Gas Exchange Measurements and Carbon Dioxide Rebreathing: A Study in Animals/Pigs*, J. Clin. Monit. (1992) 8(4):267-78.

Gedeon, A., et al., *A new method for noninvasive bedside determination of pulmonary blood flow* Med. & Biol. Eng. & Comput. (1980) 18:411-418.

Guyton, A.E., et al., *Measurement of cardiac output by the direct Fick method, In: Cardiac output and its regulation*, W.B. Saunders Company (1973) 21-39.

Kyoku, I., et al., *Measurement of cardiac output by Fick method using $CO_2$ analyzer Servo*, Kyobu Geka. Japanese Journal of Thoracic Surgery (1988) 41(12):966-70.

Lynch, J., et al., *Comparison of a modified Fick method with thermodilution for determining cardiac output in critically ill patients on mechanical ventilation*, Intensive Care Med. (1990) 16:248-51.

Mahutte, C. Kees, et al., *Relationship of Thermodilution Cardiac Output to Metabolic Measurements and Mixed Venous Oxygen Saturation*, Chest (1993) 104(4):1236-42.

Miller, D.M., et al., *A Simple Method for the Continuous Noninvasive Estimates of Cardiac Output Using the Maxima Breathing System. A Pilot Study*, Anaesth. Intens. Care (1997) 25(1):23-28.

Österlund, B., et al., *A new method of using gas exchange measurements for the noninvasive determination of cardiac output: clinical experiences in adults following cardiac surgery*, Acta Anaesthesiol Scand (1995) 39:727-32.

Sackner, Marvin A., *Measurement of cardiac output by alveolar gas exchange*, Handbook of Physiology—The Respiratory System IV, Chapter 13, 233-55.

Spalding, H. K., et al., *Carbon Dioxide ($CO_2$) Elimination Rate Accurately Predicts Cardiac Output*, Anesthesiology (1997) 87(3A) (1 page).

Sprung, Charles L., et al., *Ventricular Arrhythmias During Swan-Ganz Catheterization of the Critically Ill*, Chest (1981) 79:413-15.

Taskar, V., et al., *Dynamics of Carbon Dioxide Elimination Following Ventilator Resetting*, Chest (1995) 108:196-202.

Winkler, Tilo, et al., *Pulmonary Capillary Blood Flow by Partial $CO_2$ Rebreathing: A Simulation Study Using a Bicompartmental Model of Gas Exchange*, Crit. Care Med. (1998), vol. 26, No. 1 (Suppl.), A105, Abstract #234, (1 page).

International Search Report of Dec. 8, 2000.

Farhi, L.E., et al., "Gas Stores of the Body and the Unsteady State," O2 and CO2 Gas Stores, Mar. 1955, pp. 472-484.

Matthews, C.M.E., et al., "A Model for the Distribution and Transport of CO2 in the Body and the Ventilatory Reponse to CO2, "Respiration Physiology (1968/1969), vol. 6, pp. 45-87, North-Holland Pub. Co., Amsterdam.

Critchley et al., "A meta-analysis of studies using bias and precision statistics to compare cardiac output measurement techniques," J. Clin. Monitoring 15:85-91 (1999).

* cited by examiner

ALGORITHMS, SYSTEMS, AND METHODS FOR ESTIMATING CARBON DIOXIDE STORES, TRANSFORMING RESPIRATORY GAS MEASUREMENTS, AND OBTAINING ACCURATE NONINVASIVE PULMONARY CAPILLARY BLOOD FLOW AND CARDIAC OUTPUT MEASUREMENTS

CROSS-REFERENCE TO RELATED APPLICATIONS

This application is a continuation of application Ser. No. 10/121,219, filed Apr. 11, 2002, now U.S. Pat. No. 6,995,651, issued Oct. 18, 2005, which is a continuation-in-part of U.S. application Ser. No. 09/510,702, filed on Feb. 22, 2000, now U.S. Pat. No. 6,540,689, issued Apr. 1, 2003.

BACKGROUND OF THE INVENTION

1. Field of the Invention

The present invention relates generally to methods for noninvasively determining the pulmonary capillary blood flow or cardiac output of an individual. More specifically, the present invention relates to noninvasive methods for determining pulmonary capillary blood flow or cardiac output which account for correlation between parameters that have been measured during the same breath. In particular, the present invention includes methods for improving the correlation between carbon dioxide elimination and partial pressure of end-tidal carbon dioxide measurements.

2. Background of Related Art

So-called "rebreathing" techniques have long been used to make noninvasive determinations of both pulmonary capillary blood flow and cardiac output. In rebreathing, the respiration of an individual is monitored during both "normal" breathing, which may be either spontaneous or ventilator-induced, and when a change in the effective ventilation of the individual has occurred or been induced. In particular, in conventional rebreathing techniques, the change in effective ventilation has been induced by causing a monitored individual to breathe air or a gas mixture with an increased level of carbon dioxide relative to the amount of carbon dioxide that was inhaled by the individual during "normal" breathing.

The carbon dioxide Fick equation has long been used to determine both pulmonary capillary blood flow and cardiac output. One form of the carbon dioxide Fick equation follows:

$$\dot{Q} = VCO_2 / (c_{vCO2} - c_{aCO2}), \quad (1)$$

where $\dot{Q}$ represents blood flow (e.g., cardiac output or pulmonary capillary blood flow), $VCO_2$ is carbon dioxide elimination, $c_{vCO2}$ is carbon dioxide content of the venous blood of the monitored individual, and $c_{aCO2}$ is the carbon dioxide content of the arterial blood of the monitored individual.

When rebreathing processes are employed, the various parameters of the carbon dioxide Fick equation are typically derived from two measured signals, a measurement of the volume or flow of carbon dioxide eliminated by the body ($VCO_2$ and $\dot{V}CO_2$, respectively), which represents gases that are present in the mouth, and a measurement of the partial pressure of end-tidal carbon dioxide ($_{etCO2}$ or $p_{etCO2}$), which represents gases inside the lungs, at the alveoli. The $p_{etCO2}$ measurement correlates directly with a concentration of carbon dioxide in blood flowing past the alveoli of an individual ($c_{ACO2}$) and, therefore, is useful for determining $c_{aCO2}$ and $c_{vCO2}$.

Rebreathing is often conducted with a rebreathing circuit, through which a patient may inhale a gas mixture that includes carbon dioxide. FIG. 1 schematically illustrates an exemplary rebreathing circuit 50 that includes a tubular airway 52 that communicates air flow to and from the lungs of a patient. Tubular airway 52 may be placed in communication with the trachea of the patient by known intubation processes, or by connection to a breathing mask positioned over the nose and/or mouth of the patient. A flow meter 72, which is typically referred to as a pneumotachometer, and a carbon dioxide sensor 74, which is typically referred to as a capnometer, are disposed between tubular airway 52 and a length of hose 60, and are exposed to any air that flows through rebreathing circuit 50. Flow meter 72 and carbon dioxide sensor 74 communicate with one or more monitors 76, which are configured to monitor signals from flow meter 72 and carbon dioxide sensor 74, as known in the art. Both ends of another length of hose, which is referred to as deadspace 70, communicate with hose 60. The two ends of deadspace 70 are separated from one another by a two-way valve 68, which may be positioned to direct the flow of air through deadspace 70. Deadspace 70 may also include an expandable section 62. A Y-piece 58, disposed on hose 60 opposite flow meter 72 and carbon dioxide sensor 74, facilitates the connection of an inspiratory hose 54 and an expiratory hose 56 to rebreathing circuit 50 and the flow communication of the inspiratory hose 54 and expiratory hose 56 with hose 60. During inhalation, gas flows into inspiratory hose 54 from the atmosphere or a ventilator (not shown). During normal breathing, valve 68 is positioned to prevent inhaled and exhaled air from flowing through deadspace 70. During rebreathing, valve 68 is positioned to direct the flow of exhaled and inhaled gases through deadspace 70.

The rebreathed air, which is inhaled from deadspace 70 during rebreathing, includes air that has been exhaled by the patient (i.e., carbon dioxide-rich air).

During total rebreathing, substantially all of the gas inhaled by the patient was expired during the previous breath. Thus, during total rebreathing, the partial pressure of end-tidal carbon dioxide ($p_{etCO2}$ or $_{etCO2}$) is typically assumed to be equal to or closely related to the content of carbon dioxide in the arterial ($c_{aCO2}$), venous ($c_{vCO2}$), or alveolar ($c_{ACO2}$) blood of the patient. Total rebreathing processes are based on the assumption that neither pulmonary capillary blood flow nor the content of carbon dioxide in the venous blood of the patient ($c_{vCO2}$) changes substantially during the rebreathing process. In total rebreathing, the carbon dioxide elimination ($VCO_2$) of the patient decreases to about zero. The partial pressure of carbon dioxide in blood may be converted to the content of carbon dioxide in blood by means of a carbon dioxide dissociation curve, where the change in the carbon dioxide content of the blood ($C_{yCO2} - C_{aCO2}$) is equal to the slope(s) of the carbon dioxide dissociation curve multiplied by the measured change in end-tidal carbon dioxide ($p_{etCO2}$) as effected by a change in effective ventilation, such as rebreathing.

In partial rebreathing, the patient inhales gases that include elevated carbon dioxide levels (e.g., a mixture of "fresh" gases and gases that were exhaled during the previous breath). Thus, the patient does not inhale a volume of carbon dioxide as large as the volume of carbon dioxide that would be inhaled during a total rebreathing process. As carbon dioxide elimination ($VCO_2$) is not decreased to zero during partial rebreathing and since the carbon dioxide content of the mixed venous blood is not known during partial rebreathing, partial rebreathing processes typically employ a differential form of the carbon dioxide Fick equation to determine the pulmonary capillary blood flow or cardiac output of the patient. This differential form of the carbon dioxide Fick equation considers measurements of carbon dioxide elimination, $c_{vCO2}$, and the content of carbon dioxide in the alveolar blood of the patient ($c_{ACO2}$) during both normal breathing and the rebreathing process as follows:

$$\dot{Q}_{pcb\ BD} = \frac{VCO_{2\ B} - VCO_{2\ D}}{(c_{vCO2\ B} - c_{vCO2\ D}) - (c_{aCO2\ B} - c_{aCO2\ D})},\quad (2)$$

where $VCO_{2\ B}$ and $VCO_{2\ D}$ are the carbon dioxide production of the patient before rebreathing and during the rebreathing process, respectively, $c_{vCO2\ B}$ and $c_{vCO2\ D}$ are the content of $CO_2$ of the venous blood of the patient before rebreathing and during the rebreathing process, respectively, and $c_{aCO2\ B}$ and $c_{aCO2\ D}$ are the content of $CO_2$ in the arterial blood of the patient before rebreathing and during rebreathing, respectively.

Again, with a carbon dioxide dissociation curve, the measured $p_{etCO2}$ can be used to determine the change in content of carbon dioxide in the blood before and during the rebreathing process. Accordingly, the following equation can be used to determine pulmonary capillary blood flow or cardiac output when partial rebreathing is conducted:

$$\dot{Q} = \Delta VCO_2/s\Delta p_{etCO2}.\quad (3)$$

Accordingly, a plot of $VCO_2$ against $p_{etCO2}$ during both "normal" respiration and rebreathing is known to provide an indicator of the pulmonary capillary blood flow of an individual. The individual's pulmonary capillary blood flow is about equal to the negative slope (i.e., negative one multiplied by the slope) of the resulting line or curve.

Alternative differential Fick methods of measuring pulmonary capillary blood flow or cardiac output have also been employed. Such differential Fick methods typically include a brief change of $p_{etCO2}$ and $VCO_2$ in response to a change in effective ventilation. This brief change can be accomplished by adjusting the respiratory rate, inspiratory and/or expiratory times, or tidal volume. A brief change in effective ventilation may also be effected by adding $CO_2$, either directly or by rebreathing. An exemplary differential Fick method that has been employed, which is disclosed in Gedeon, A. et al. in 18 MED. & BIOL. ENG. & COMPUT. 411–418 (1980), includes a period of increased ventilation followed immediately by a period of decreased ventilation.

Carbon dioxide elimination ($VCO_2$) is typically measured as the difference between the amount of carbon dioxide inhaled and the amount of carbon dioxide exhaled, with the amount of carbon dioxide exhaled usually being greater than that inhaled. The carbon dioxide elimination of a patient is typically measured over the course of a breath by the following, or an equivalent, equation:

$$VCO_2 = \int_{breath} V \times f_{CO2} dt,\quad (4)$$

where V is the measured respiratory flow and $f_{CO2}$ is the substantially simultaneously detected carbon dioxide signal, or fraction of the respiratory gases that comprises carbon dioxide or "carbon dioxide fraction."

Prior to rebreathing, the amount of carbon dioxide eliminated ($VCO_2$) by the patient, through his or her lungs, is much greater than the amount of $CO_2$ inhaled by the patient. In rebreathing, although the amount of carbon dioxide inhaled by the individual and the amount of carbon dioxide exhaled by the individual both typically increase, the $VCO_2$ measurement typically decreases. The difference between the amounts of carbon dioxide inhaled and eliminated is reduced by an amount that corresponds to the increased amount of carbon dioxide inhaled by the patient. Detection of the change in $VCO_2$ that may occur with changes in the effective ventilation of an individual may be somewhat delayed due to the dampening effect of the carbon dioxide stores of the individual's lungs. For example, at the beginning of rebreathing, a significant portion of the increased amount of carbon dioxide inhaled by the individual is absorbed by the carbon dioxide stores. If the amount of carbon dioxide inhaled during rebreathing is significantly increased, then a significant decrease will be seen in the difference between the amounts of carbon dioxide inhaled and eliminated, while this difference will be much less if the amount of carbon dioxide inhaled during rebreathing is only slightly greater than that inhaled during the patient's normal respiration.

$VCO_2$ is the first of the two signals (i.e., $VCO_2$ and $p_{etCO2}$) to accurately reflect rebreathing-induced changes. When rebreathing is initiated, the amount of carbon dioxide that is inhaled is increased. Prior to rebreathing, the lungs of the patient have been exposed to typical amounts of carbon dioxide, such as those experienced during normal respiration. Initially, some of the increased carbon dioxide that is inhaled during rebreathing is absorbed by the carbon dioxide stores of the lungs, including the functional residual capacity (FRC), which comprises stored gases, and lung tissues. Thus, only a portion of the increased amount of inhaled carbon dioxide initially makes its way to the alveoli, or air sacs, of the lungs, where gases exit and are absorbed by the blood. It only takes a short amount of time for the carbon dioxide stores of the lungs to equilibrate to the increased amount of carbon dioxide being inhaled. When such equilibration occurs, substantially all of the increase in the amount of carbon dioxide inhaled is realized in the alveoli. At that point in time, the full reduction in the difference between the amount of carbon dioxide inhaled by the patient and the amount of carbon dioxide eliminated by the patient may be noninvasively measured.

Assuming the increased amount of carbon dioxide inhaled by the individual is sufficient to quickly maximize the concentration of carbon dioxide in the carbon dioxide stores, the amount of carbon dioxide exhaled by the individual in the same breath may be used to accurately determine the $VCO_2$ of the patient.

The partial pressure of end-tidal carbon dioxide ($p_{etCO2}$ or $_{etCO2}$), after correcting for any deadspace, is typically assumed to be approximately equal to the partial pressure of carbon dioxide in the alveoli ($P_ACO_2$) of the patient or, if there is no intrapulmonary shunt, the content of $CO_2$ in the blood flowing past the alveoli ($c_{ACO2}$), as well as the $CO_2$ content of oxygenated blood downstream from the alveoli ($c_{aCO2}$).

The $p_{etCO2}$ measurement, which represents a measurement of carbon dioxide in the lungs of an individual, is typically not representative of the true gases that are present in the lungs at the time the measurement is taken. This is because, in rebreathing, the increased amount of carbon dioxide inhaled does not go directly to the alveoli. Rather, the carbon dioxide stores of the lungs, including the functional residual capacity (deadspace) and lung tissues, which do not participate directly in respiration, act as a buffer or filter. This filtering action includes the absorption and release of carbon dioxide in a manner that depends upon the amount of carbon dioxide in gases that are directly involved in respiration. Accordingly, when rebreathing first begins, a significant portion of the increased amount of carbon dioxide in the inhaled gases is initially absorbed into the carbon dioxide stores. Once the amount of carbon dioxide in the carbon dioxide stores and the amount of carbon dioxide in the "rebreathed" gases (including inspiratory and expiratory gases) equilibrate with one another, the amount of carbon dioxide within the lungs, including $p_{etCO2}$, may be accurately detected. The converse is also true: when "normal" respiration is recommenced, the reduced amount of carbon dioxide in the expired gases is not immediately realized in an externally obtained, noninvasive respiratory measurement. Rather, carbon dioxide is released from the carbon dioxide stores of the lungs until the amount of carbon dioxide in the carbon dioxide stores equilibrates with the amounts of carbon dioxide in the inspiratory and expiratory gases. Only after such equilibration has taken place may accurate measurements of gases within the lungs, such as $p_{etCO2}$, be noninvasively obtained. Accordingly, at the start of both a rebreathing phase and "normal" breathing following a rebreathing phase, an immediate change in $p_{etCO2}$ is typically not seen.

Once the increase in the amount of inhaled carbon dioxide is realized at the level of the alveoli, the content of $CO_2$ in the blood must increase correspondingly for carbon dioxide to be released from the blood as the blood flows past the alveoli. Thus, an additional period of time is required before the amount of carbon dioxide in the blood increases to a level which will facilitate release of the increased amount of carbon dioxide from the blood and an increase in the amount of carbon dioxide in the blood, which may be determined from a $p_{etCO2}$ measurement, may be detected. Thus, the accuracy of the $p_{etCO2}$, relative to the point in time at which the measurement is obtained relative to the initiation of rebreathing, lags behind the time-accuracy of the $VCO_2$ measurement. This lag typically amounts to a period of time that corresponds to one or two breaths.

Following rebreathing, the amount of carbon dioxide inhaled by a patient is decreased. The carbon dioxide stores in the lungs equilibrate to the new amount of carbon dioxide being inhaled by releasing carbon dioxide. Consequently, while the carbon dioxide levels of the carbon dioxide stores of the lungs are equilibrating, the amount of carbon dioxide exhaled by the patient remains at an elevated level for a period of time following even a significant decrease in the amount of carbon dioxide inhaled by the patient.

Likewise, during equilibration of the carbon dioxide stores of a patient's lungs, the amount of carbon dioxide within the alveoli remains greater than that in the air or other gas mixture inhaled by the patient. Thus, carbon dioxide levels in the blood remain elevated. Once the carbon dioxide stores in the lungs of the patient begin to decrease and the amount of carbon dioxide within the alveoli begins to resemble the amount of carbon dioxide in the air or gases that have been inhaled by the patient, the high levels of carbon dioxide that have accumulated in the blood may be more readily released therefrom. Accordingly, following rebreathing, the amount of carbon dioxide in the blood flowing past the alveoli of the patient will initially remain high, as may be evidenced by relatively high $p_{etCO2}$ measurements. As the excess carbon dioxide that is trapped in the blood during rebreathing is gradually released therefrom, the amount of carbon dioxide in the alveolar blood of the patient decreases to a "normal" level.

It may be said that the carbon dioxide stores of a patient's lungs filter the $p_{etCO2}$ signal to a much greater extent than the $VCO_2$ signal is filtered by the carbon dioxide stores. Because $VCO_2$ signals typically respond to changes in the effective ventilation of a patient, such as rebreathing and nonrebreathing states, about one or two breaths before the $p_{etCO2}$ signal(s) for the same breath(s) will respond to such changes, $VCO_2$ and $p_{etCO2}$ signals that are obtained during the same breath do not correlate well with one another. Accordingly, a $VCO_2$ signal may lead a $p_{etCO2}$ signal by a time differential equal to the duration of about one or two breaths. Thus, at a particular point in time, the $VCO_2$ and $p_{etCO2}$ signals do not correspond to one another. Stated another way, the accuracy of the $p_{etCO2}$ measurement lags that of the $VCO_2$ measurement by a time duration equal to the length of a breath or two. As these values are often used to noninvasively determine pulmonary capillary blood flow or cardiac output, the lack of correspondence between these values may lead to inaccuracies in the pulmonary capillary blood flow or cardiac output determination.

The correlation between the $p_{etCO2}$ and $VCO_2$ signals may be quantified by a so-called "correlation coefficient" ($r^2$), where a value of 1 indicates complete correlation between the two signals and lesser values represent correspondingly lesser degrees of correlation. This is evidenced when $VCO_2$ signals are plotted against $c_{aCO2}$ signals, such as the data shown in FIGS. 2A and 2B respectively, with the result appearing as an open loop, as depicted in the plot of FIG. 4, rather than the ideal straight line depicted in FIG. 3. As it is difficult to accurately assign a slope to a loop, it is difficult to accurately determine pulmonary capillary blood flow from a plot of noninvasively obtained $p_{etCO2}$-based $c_{aCO2}$ signals against $VCO_2$ signals.

Upon the start of rebreathing, the flow of carbon dioxide eliminated at the mouth ($\dot{V}_M CO_2$) almost instantaneously drops to a lower level, while the plot of $p_{etCO2}$ goes through a transitional period before reaching the steady-state plateau at which it stays until the end of rebreathing. The trend plots of alveolar $CO_2$ content ($C_{ACO2}$) and the volume of $CO_2$ excreted from the blood into the alveoli ($\dot{V}_B CO_2$) from the carbon dioxide Fick equation (equation (1)) should follow the same shape (albeit inverted, due to the negative slope) as that of FIG. 3. However, $VCO_2$ is not measured at the alveolar level ($\dot{V}_B CO_2$), but at the mouth ($\dot{V}_M CO_2$).

In addition, measurements that are taken during spurious breaths, or breaths which do not provide information relevant to pulmonary capillary blood flow or cardiac output, may act as noise that introduces inaccuracy into the noninvasive pulmonary capillary blood flow or cardiac output determination.

When equation (4) is employed to calculate the $VCO_2$ of a patient from the respiratory flow and carbon dioxide fraction measurements over an entire breath, such miscorrelation or noise-induced inaccuracies in either the expiratory flow, the inspiratory flow, or both may cause inaccuracies in the determination of $VCO_2$ or inconsistencies between $VCO_2$ determinations.

The inventors are not aware of a method for using a model of the lung which includes estimation, evaluation, or use of the carbon dioxide stores of the lung to transform, modify, or filter one or more noninvasively obtained respiratory signals to increase the correlation of each filtered or modified respiratory signal with at least one other noninvasively obtained respiratory signal.

SUMMARY OF THE INVENTION

The present invention includes correlating an indicator of a change in $VCO_2$, which, for simplicity, is hereinafter referred to as a "change in $VCO_2$," to a corresponding change in an indicator of the content of carbon dioxide in the blood. Examples of changes in $VCO_2$ that may be obtained and transformed in accordance with teachings of the present invention include, without limitation, a change in the net volume of $CO_2$ (between expiratory and inspiratory $CO_2$), a change in the inspiratory volume of $CO_2$, and a change in another component of inspired or expired air (e.g., a change in oxygen). Examples of changes in an indicator of the content of $CO_2$ in the blood of an individual include, but are not limited to, $c_{vCO2}$, $c_{ACO2}$, $c_{aCO2}$, and $p_{etCO2}$, as well as surrogates and equivalents of any of the foregoing. Correlation in accordance with teachings of the present invention may be used in accurately and noninvasively measuring the pulmonary capillary blood flow or cardiac output of an individual.

In an exemplary aspect of the present invention, one or both of the $VCO_2$ and $p_{etCO2}$ signals that have been taken at different respiratory or ventilatory states may be transformed or filtered, such as over the course of a change in the effective ventilation of an individual (e.g., during a rebreathing process). Transformation or filtering in accordance with teachings of the present invention effectively counteracts any dampening by the carbon dioxide stores in the lungs of an individual over the course of a change in the effective ventilation of the individual and substantially correlates $VCO_2$ and $p_{etCO2}$ signals that correspond, in time, to one another. Stated another way, the shapes of corresponding $VCO_2$ and $p_{etCO2}$ or $c_{CO2}$ signals may be compared with one another to estimate the size or effect of the lung stores on the accuracies of these measurements and, thus, to determine an appropriate transformation coefficient, or filter coefficient, for increasing the accuracy of one or more of the $VCO_2$, $p_{etCO2}$, and $c_{CO2}$ signals. Methods of the present invention may, therefore, substantially eliminate any lag time that may be caused by carbon dioxide stores of an individual's lungs and that may exist between changes in the amounts of respiratory gases at the mouth and those in the lungs.

By way of example only and not to limit the scope of the present invention, the $p_{etCO2}$ signal, which tends to be dampened, or filtered, by the carbon dioxide stores of an individual's lungs to a greater degree than a $VCO_2$ signal obtained from respiration of the individual, may be "sped up" to match a corresponding $VCO_2$ signal. The $p_{etCO2}$ signal may be "sped up" by amplifying the signal.

As another example, the $VCO_2$ or $\dot{V}CO_2$ signal may be "slowed down." Slowing down of the $VCO_2$ signal may be accomplished by use of a signal from at least one previous or subsequent breath, such as the breath that immediately preceded that from which a "corresponding" $p_{etCO2}$ signal has been obtained. Use of this technique may facilitate the effective elimination of any noise that may be present in a $VCO_2$ or $\dot{V}CO_2$ signal.

As the difference in the rates at which the carbon dioxide stores of an individual's lungs dampen, or filter, the $p_{etCO2}$ and $VCO_2$ signals is taken into consideration in the method of the present invention, it may be said that the method of the present invention employs a model of the lung of an individual to measure the individual's $p_{etCO2}$.

The volume of carbon dioxide stores in the lungs of the individual, including the so-called functional residual capacity, or gas volume of the lungs that does not directly participate in respiration, and the volume of carbon dioxide absorbed by the tissues of the lung are estimated to provide a correlation coefficient (referring to the correlation between simultaneously obtained $VCO_2$ and $p_{etCO2}$ signals), or $r^2$ value, in which the measured $VCO_2$ and $p_{etCO2}$ values may be plotted in a substantially linear fashion. Initially, by way of example only, this volume may comprise an estimate based on a size of the patient or, simply, a prespecified starting point. The estimated volume of carbon dioxide stores may be adjusted. If the adjustments improve the linearity of the $VCO_2$ vs. $p_{etCO2}$ plot, the adjustments are being made in the proper manner. If the linearity of the plotted values decreases, it can readily be determined that different, opposite adjustments may improve the linearity with which $VCO_2$ and $p_{etCO2}$ are plotted against one another.

It may be assumed that the state of the lungs during a particular breathing cycle (e.g., during an $n^{th}$ breath during the course of causing a change in the effective ventilation of an individual) closely resembles the state of the lungs during the immediately preceding breathing cycle (e.g., during the $n-1^{th}$ breath during the course of causing a change in the effective ventilation of the individual). Accordingly, when a subsequent breathing cycle begins, the initial estimate of the carbon dioxide stores may be the same or substantially the same as the final estimate of the volume of carbon dioxide stores used during the previous breathing cycle.

It is possible, however, that the volume of the carbon dioxide stores of the lungs of an individual may change over even relatively short periods of time. For example, movement by the individual from one position to another may cause the pressure within the lungs to change, which may also result in a change in the volume of the carbon dioxide stores of the lungs. The effect of such a change may be estimated and accounted for in the initial estimate of the carbon dioxide stores for a subsequent breathing cycle, or the initial estimate of the carbon dioxide stores may remain the same as that for the previous breathing cycle and be quickly adjusted to compensate for such a change in the volume of the carbon dioxide stores.

It is also within the scope of the present invention to adjust previously obtained measurements when a more accurate estimate of the volume of carbon dioxide stores in the lungs, or lung model, is obtained.

Although the methods described herein are in reference to two measurements and two corresponding compartments of the respiratory tract of an individual, like methods which involve measurements that correspond to more than two parts of an individual's respiratory tract and that match measured signals to particular, common points in time are also within the scope of the present invention.

As a result of transforming or filtering one or both of the $VCO_2$ and $p_{etCO2}$ signals obtained over a change in the effective ventilation of an individual in accordance with teachings of the present invention, it may be possible to determine the location and, thus, the slope of a best-fit line for a plot of the $VCO_2/p_{etCO2}$ signals, or data points, with greater precision and accuracy, leading to a more accurate estimation of one or both of the pulmonary capillary blood flow and cardiac output of the individual.

While the foregoing type of transformation is conducted in the time domain, corresponding types of transformation, such as a Fourier transform, may be conducted in the frequency domain.

Additionally, the present invention includes methods, systems, and algorithms for estimating the volume of the carbon dioxide stores of an individual's lungs, as well as methods, systems, and algorithms for determining the amount of carbon dioxide flowing into and out of the carbon dioxide stores and for evaluation of the volume of the FRC of the individual's lungs.

Other features and advantages of the present invention will become apparent to those of ordinary skill in the art through a consideration of the ensuing description, the accompanying drawings, and the appended claims.

BRIEF DESCRIPTION OF THE SEVERAL VIEWS OF THE DRAWINGS

In the drawings, which depict exemplary embodiments of various aspects of the present invention.

DETAILED DESCRIPTION OF THE INVENTION

The rate at which blood flows past a particular alveolus of an individual's lungs may be calculated as the ratio of the flow of $CO_2$ leaving the blood ($\dot{V}_B CO_2$), or carbon dioxide excretion from the blood, to the $CO_2$ content difference between the unoxygenated, upstream blood approaching the alveolus ($c_{vCO2}$) and oxygenated, downstream blood leaving the alveolus ($c_{aCO2}$). This is the basis for the carbon dioxide form of the Fick equation that follows:

$$\dot{Q} = \frac{\dot{V}_B CO_2}{c_{vCO2} - c_{aCO2}} \quad (5)$$

As gas exchange occurs at the alveolus, the content of $CO_2$ in blood at the alveolus ($c_{ACO2}$) is assumed to be substantially the same as the content of $CO_2$ in blood leaving the alveolus ($c_{aCO2}$), assuming that none of the blood is shunted away from the alveolus. Thus, $c_{ACO2}$ may be substituted for $c_{aCO2}$ in equation (5).

Substituting $c_{ACO2}$ for $c_{aCO2}$ and rearranging equation (5) for a calculation of $\dot{V}_B CO_2$ results in the following:

$$\dot{V}_B CO_2 = -\dot{Q} c_{ACO2} + \dot{Q} c_{vCO2}. \quad (6)$$

In a plot of $\dot{V}_B CO_2$ signals (y-axis) against $c_{ACO2}$ signals (x-axis) taken at various points during and before or after a change in the effective ventilation of an individual, it can be seen from the standard equation for a line, y=mx+b, that the slope (y) of a line taken through the various plotted data points will be $-\dot{Q}$, while $\dot{Q} c_{vCO2}$ is the intercept (b).

Equations (5) and (6) are based on the rate at which carbon dioxide leaves, or is eliminated from, the blood at the alveoli ($\dot{V}_B CO_2$). If the flow of $CO_2$ from the blood into the alveoli, or carbon dioxide excretion ($\dot{V}_B CO_2$), could be measured and plotted against $c_{ACO2}$ during rebreathing, data from every breath, including transitional data points, would fall on the line defined by equation (6). Carbon dioxide excretion ($\dot{V}_B CO_2$) is not measured at the alveolar level, however. Rather, it is measured as carbon dioxide elimination ($\dot{V}_M CO_2$) at the mouth. The carbon dioxide elimination measured at the mouth ($\dot{V}_M CO_2$) is the sum of the flow of $CO_2$ excreted from the blood ($\dot{V}_B CO_2$) and the flow of $CO_2$ into or out of the $CO_2$ stores ($\dot{V}_{STORES} CO_2$). Thus, $$\dot{V}_B CO_2 = \dot{V}_M CO_2 - \dot{V}_{STORES} CO_2. \quad (7)$$

Figure 5:
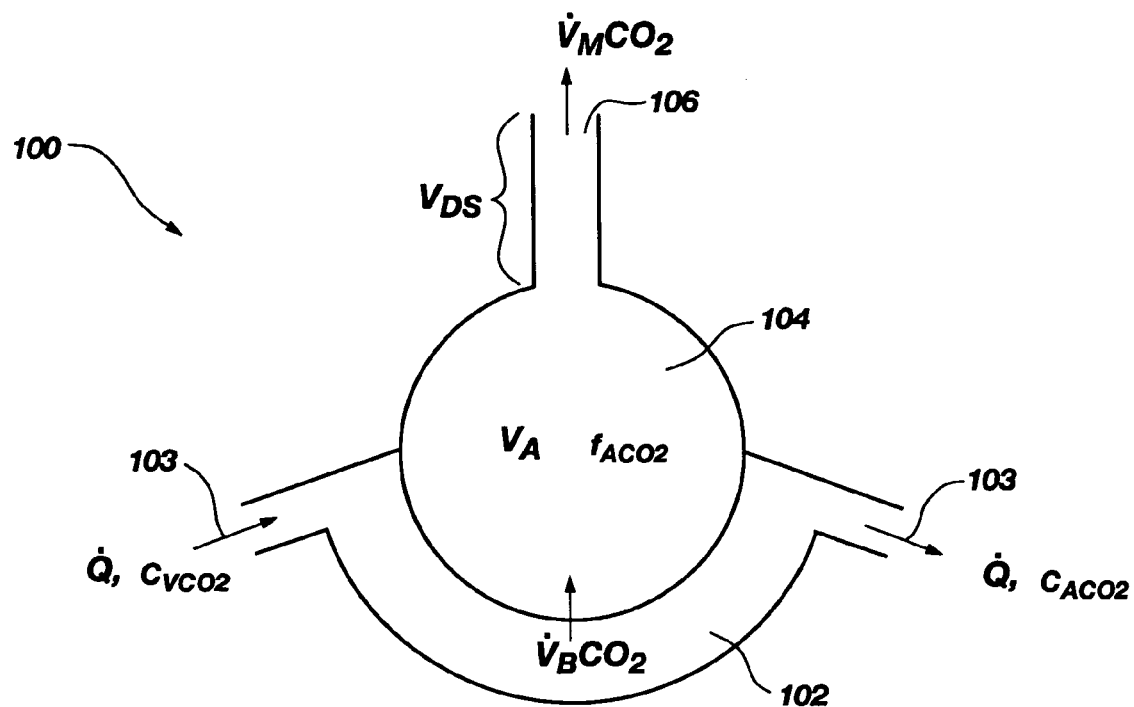
FIG. 5 is a schematic representation of an alveolus of an individual, illustrating the locations at which various respiratory and blood gas parameters may be determined.

At the beginning of rebreathing, the $CO_2$ stores of an individual's lungs absorb some of the increased $CO_2$, causing $\dot{V}_B CO_2$ to change more gradually than $\dot{V}_M CO_2$ changes. The $CO_2$ stores of an individual's lungs may be evaluated by use of a model of the lung, such as the simple model of the lung depicted in FIG. 5, in which a single alveolus 100 and a corresponding pulmonary capillary 102 represent the lung. The direction in which blood flows through pulmonary capillary 102 is represented by arrows 103. The mouth of an individual is represented at reference 106. In the model of FIG. 5, the carbon dioxide stores of the lung are depicted, for the purpose of simplicity, as comprising the physical gas volume 104 of the alveolus ($V_A$). As known in the art, $V_A$ is related to the functional residual capacity ($V_{FRC}$) of the lung and to tidal volume ($V_T$). In addition to the illustrated contributors to the $CO_2$ stores of the lung, $CO_2$ may be distributed within other stores, such as the alveolar tissues and other tissues of the lung. In addition, the lung model shown in FIG. 5 omits $V_T/V_Q$ mismatch and shunting of blood. For modeling purposes, the mixing of air within the alveolus (including inspired gases, $CO_2$ escaping from the blood, flow of $CO_2$ into and out of the $CO_2$ stores, and gases within the alveolus) is assumed to occur instantaneously. The effective volume of the $CO_2$ stores of an individual's lungs are denoted herein as "$V_A^*$."

Figure 6:
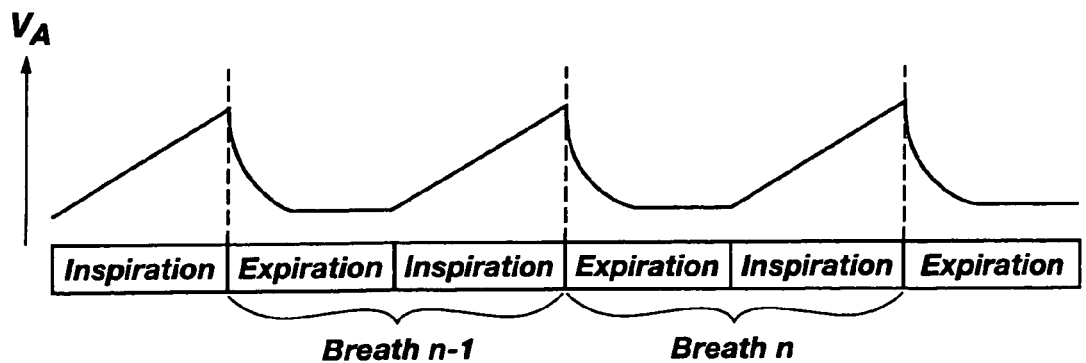
FIG. 6 is a graph that illustrates the volume of gases in the carbon dioxide stores of a respiratory tract of an individual ($V_A$) during a series of respiratory cycles, or breaths.

In the method of the present invention, a model of the lung, such as that depicted in FIG. 5, may be evaluated on a breath-by-breath basis. By way of example only, a breath may be delineated as the period from the end of one inspiration to the end of the next inspiration, as illustrated in FIG. 6. In addition, FIG. 6 depicts an example of the effective volume of $CO_2$ stores in the individual's respiratory tract (e.g., lungs) during the course of respiration.

If the effective volume of $CO_2$ stores ($V_A^*$) does not change from breath to breath, the flow into and out of the $CO_2$ stores from one breath to the next may be expressed as a change in alveolar $CO_2$ fraction ($f_ACO_2$) (i.e., the fraction of gases in the alveolus that comprise $CO_2$), or the difference between $f_ACO_2$ for a particular breath ($f_ACO_2(n)$) and $f_ACO_2$ for the previous breath $f_ACO_2(n-1)$. Substituting the change in alveolar $CO_2$ fraction, along with a consideration of the volume of the $CO_2$ stores of the individual's lungs and the individual's respiratory rate (RR), for the flow of $CO_2$ into and out of the carbon dioxide stores ($\dot{V}_{STORES}CO_2$) in equation (7) results in the following:

$$\dot{V}_BCO_2(n) = \dot{V}_MCO_2(n) + V_A^*(n)[f_ACO_2(n)-f_ACO_2(n-1)]RR, \quad (8)$$

where "n" denotes the current or most recent breath and "n−1" denotes the previous breath. Equation (8) is particularly useful for estimating $\dot{V}_BCO_2$ from $\dot{V}_MCO_2$ measurements that are obtained during the transition from nonrebreathing, or "normal" breathing, to rebreathing. An estimate of $\dot{V}_BCO_2$ is denoted herein as $\hat{\dot{V}}_BCO_2$ and may be substituted for $\dot{V}_BCO_2$ in equation (8).

As it may be assumed that the alveolar $CO_2$ fraction ($f_{ACO2}$) is proportional to $p_{etCO2}$, which may be measured by use of a capnometer, the $p_{etCO2}$ measurement may be used, as known in the art, to obtain an $f_{ACO2}$ value for each breath.

Figure 7:
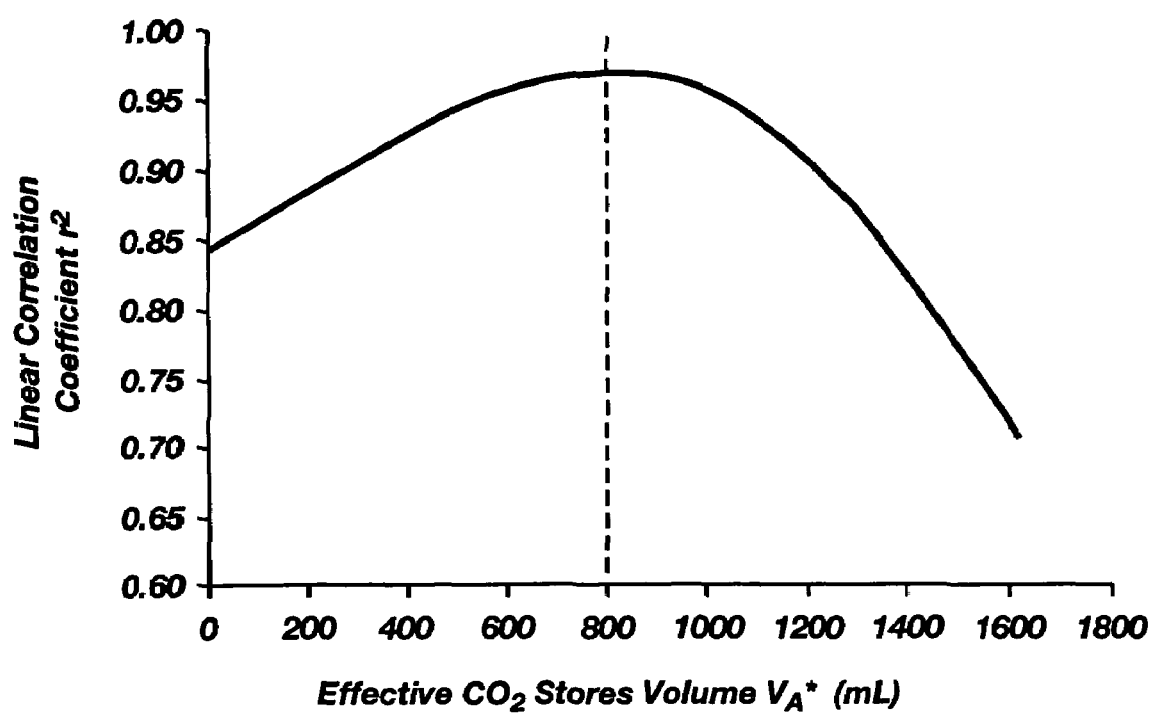
FIG. 7 is a graph representing an exemplary relationship between an estimate of the volume of gases in the carbon dioxide stores in a respiratory tract of an individual ($V_A^*$) and a correlation coefficient ($r^2$) between corresponding $\dot{V}_B CO_2$ and $c_{ACO2}$ data.

The effective volume of the $CO_2$ stores ($V_A^*$) may be adaptively estimated, such as by using the linear correlation between $\hat{\dot{V}}_BCO_2$ from equation (8), substituting $\hat{V}_A^*$ for $V_A^*$, and $c_{ACO2}$ as a guide (see equation (6)). The more accurately the estimated effective alveolus volume $\hat{V}_A^*$ reflects the actual effective alveolus volume $V_A^*$, the closer the data points of a plot of $\hat{\dot{V}}_BCO_2$ against $c_{ACO2}$ over the course of a change in the effective ventilation of an individual will be to a line representative of the actual pulmonary capillary blood flow or cardiac output of the individual. The ideal value for $\hat{V}_A^*$ may, therefore, be determined as the value that results in the best linear fit between the plotted data ($c_{ACO2}$ against $\hat{\dot{V}}_BCO_2$) and, thus, a maximized correlation coefficient, or $r^2$ value. By way of example only, an adaptive, iterative, or search algorithm of a type known in the art may be used to determine $\hat{V}_A^*$ for which the correlation coefficient, or $r^2$, is maximized. The graph of FIG. 7 shows an example of a $\hat{V}_A^*$ value at which $r^2$ is maximized.

Once an accurate $\hat{V}_A^*$ value has been obtained, $V_{FRC}$ may also be estimated or determined, as known in the art.

Equation (8) may be rewritten, as follows, to reflect the use of $\hat{V}_A^*$ as an estimate for $V_A^*$:

$$\hat{\dot{V}}_BCO_2(n) = \dot{V}_MCO_2(n) + \hat{V}_A^*(n)[f_ACO_2(n)-f_ACO_2(n-1)]RR. \quad (9)$$

The foregoing approach (particularly, the use of equation (9)) works well when an individual is mechanically ventilated (i.e., on a respirator), in which case the respiratory rate and tidal volume of the individual's respiration are typically substantially stable, which provides for a "clean" $f_ACO_2$ signal.

During mixed or spontaneous ventilation, it may be desirable to eliminate any noise that may occur in the $f_ACO_2$ signal when equation (9) is used, as such noise may result in an inaccurate estimation of $\hat{\dot{V}}_BCO_2$. An algorithm that is less sensitive to noise than equation (9) may, therefore, also be useful for estimating $\hat{\dot{V}}_BCO_2$.

Assuming that pulmonary capillary blood flow and cardiac output do not change from one breath to the next, the carbon dioxide Fick equation (equation (5)) may be rewritten for two successive breaths:

$$\dot{Q} = \frac{\dot{V}_BCO_2(n-1)}{c_{vCO2}(n-1) - c_{ACO2}(n-1)} = \frac{\dot{V}_BCO_2(n)}{c_{vCO2}(n) - c_{ACO2}(n)} \quad (10)$$

Further, assuming that $c_{vCO2}$ does not change from one breath to the next, equation (10) may be simplified to:

$$\dot{Q} = \frac{\dot{V}_BCO_2(n-1) - \dot{V}_BCO_2(n)}{c_{ACO2}(n) - c_{ACO2}(n-1)} \quad (7)$$

Measurements of the $CO_2$ fraction of gases in an individual's alveoli ($f_ACO_2$) may be used in place of the $c_{ACO2}$ measurements of equation (11) when the slope of the $CO_2$ dissociation curve ($s_{CO2}$), a standard curve which illustrates the rate at which $CO_2$ molecules dissociate from the hemoglobin molecules of red blood cells, and barometric pressure ($p_{baro}$) are also taken into consideration, as known in the art. Accordingly, equation (11) may be rewritten as follows:

$$\dot{Q} = \frac{\dot{V}_BCO_2(n-1) - \dot{V}_BCO_2(n)}{s_{CO2}p_{baro}[f_ACO_2(n) - f_ACO_2(n-1)]} \quad (12)$$

Solving this expression for the difference in $CO_2$ fractions ($f_ACO_2(n)-f_ACO_2(n-1)$) yields:

$$f_ACO_2(n) - f_ACO_2(n-1) = \frac{\dot{V}_BCO_2(n-1) - \dot{V}_BCO_2(n)}{s_{CO2}p_{baro}\dot{Q}} \quad (13)$$

Substitution of equation (13) into equation (9) results in:

$$\hat{\dot{V}}_BCO_2(n) = \dot{V}_MCO_2(n) + \frac{RR\,\hat{V}_A^*(n)}{s_{CO2}p_{baro}\dot{Q}}\left[\hat{\dot{V}}_BCO_2(n-1) - \hat{\dot{V}}_BCO_2(n)\right] \quad (14)$$

This expression can now be solved for $\dot{V}_B CO_2(n)$:

$$\hat{\dot{V}}_B CO_2(n) = \frac{1}{1+\frac{RR\hat{V}_A^*(n)}{s_{CO2}p_{baro}\dot{Q}}}\dot{V}_M CO_2(n) + \frac{\frac{RR\hat{V}_A^*(n)}{s_{CO2}p_{baro}\dot{Q}}}{1+\frac{RR\hat{V}_A^*(n)}{s_{CO2}p_{baro}\dot{Q}}}\hat{\dot{V}}_B CO_2(n-1) \quad (15)$$

Structurally, this result represents a first order single-pole low pass filter of the form $$\hat{V}_B CO_2(n) = (1-\alpha)\dot{V}_M CO_2(n) + \alpha \hat{V}_B CO_2(n-1), \quad (16)$$

where $\alpha$, the transformation coefficient, may be represented as $$\frac{\frac{RR\hat{V}_A^*(n)}{s_{CO2}p_{baro}\dot{Q}}}{1+\frac{RR\hat{V}_A^*(n)}{s_{CO2}p_{baro}\dot{Q}}}$$

Of course, $\dot{Q}$ is an unknown variable, which is not actually necessary for determining either $\alpha$ or $\hat{V}_A^*$. Equation (15) merely proves that equation (16) is equivalent to a physiologic model of the lungs of an individual by which the relationship between $VCO_2$, $c_{CO2}$, and $\dot{V}_{STORES}CO_2$ may be evaluated to accurately determine pulmonary capillary blood flow or cardiac output.

The transformation coefficient ($\alpha$) in equation (16) may be determined iteratively, by using an initial $\alpha$ value, then progressively increasing and/or decreasing the $\alpha$ value to determine the $\alpha$ value that provides an optimal correlation coefficient ($r^2$), or provides for a plot of $VCO_2$ values against $p_{etCO2}$ or $c_{CO2}$ values with the greatest linearity (as opposed to an open loop). Other alternative methods for determining an optimal $\alpha$ value include, without limitation, rote searching, global searching, gradient searching (e.g., use of a gradient descent search algorithm), use of a least mean squares algorithm, use of other predetermined equations or sets of predetermined equations, use of a truly adaptive filtering technique, and use of other techniques to determine the optimal $\alpha$ value, as known in the art. Once an optimal $\alpha$ value has been determined, equation (16) may be used in a determination of the pulmonary capillary blood flow or cardiac output of an individual.

The algorithm of equation (16) comprises a simple model of the lung that may be used to calculate the amount of $CO_2$ that flows into and out of the carbon dioxide stores of the lungs on a "breath-to-breath" basis. A determination of $\hat{V}_B CO_2(n)$ in accordance with either of these models may be used in equation (9) and, of course, when a change in the effective ventilation of an individual has occurred, to determine the pulmonary capillary blood flow or cardiac output of the individual.

Figure 1:
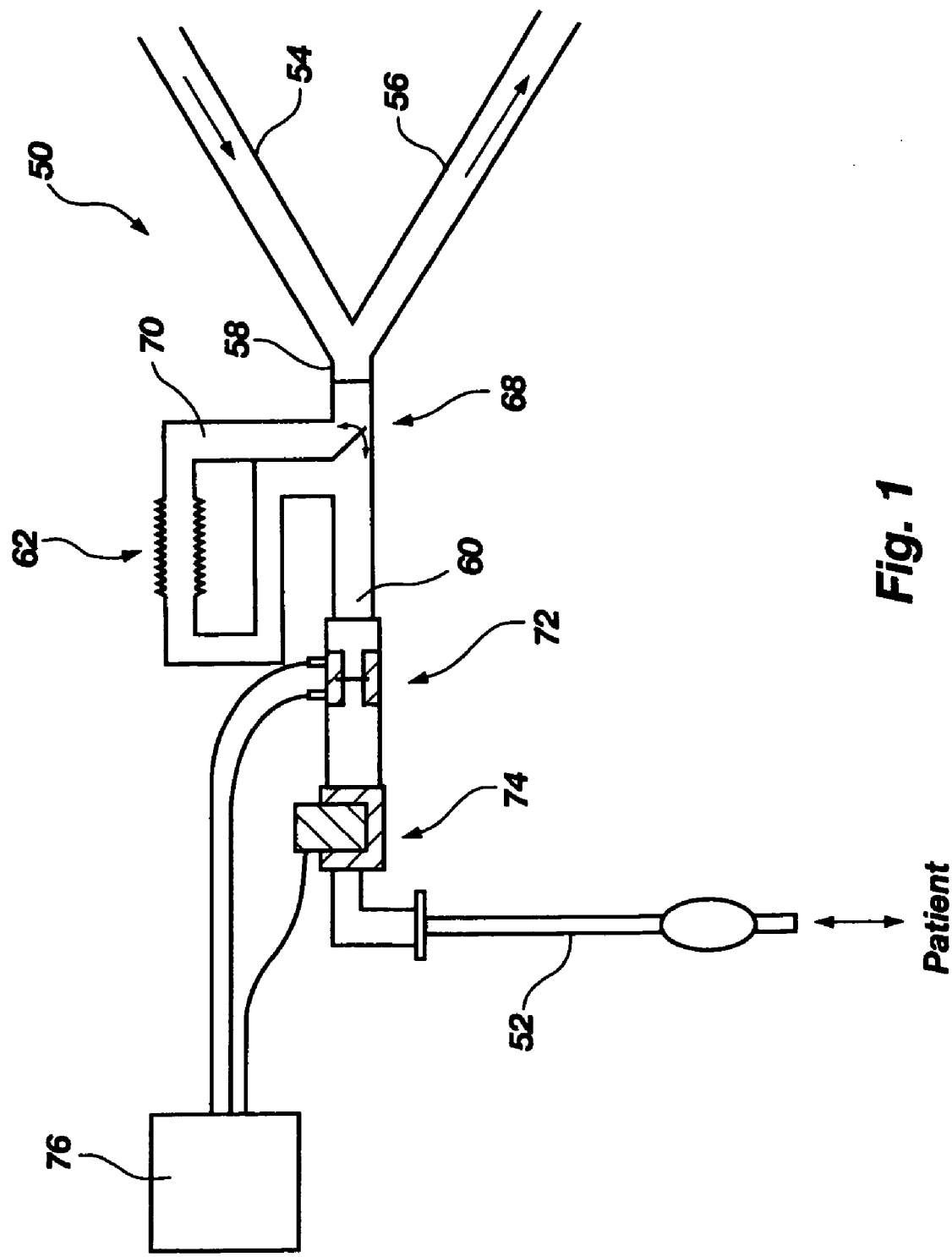
FIG. 1 is a schematic representation of an exemplary rebreathing circuit that may be employed with the methods of the present invention.
Figure 2A:
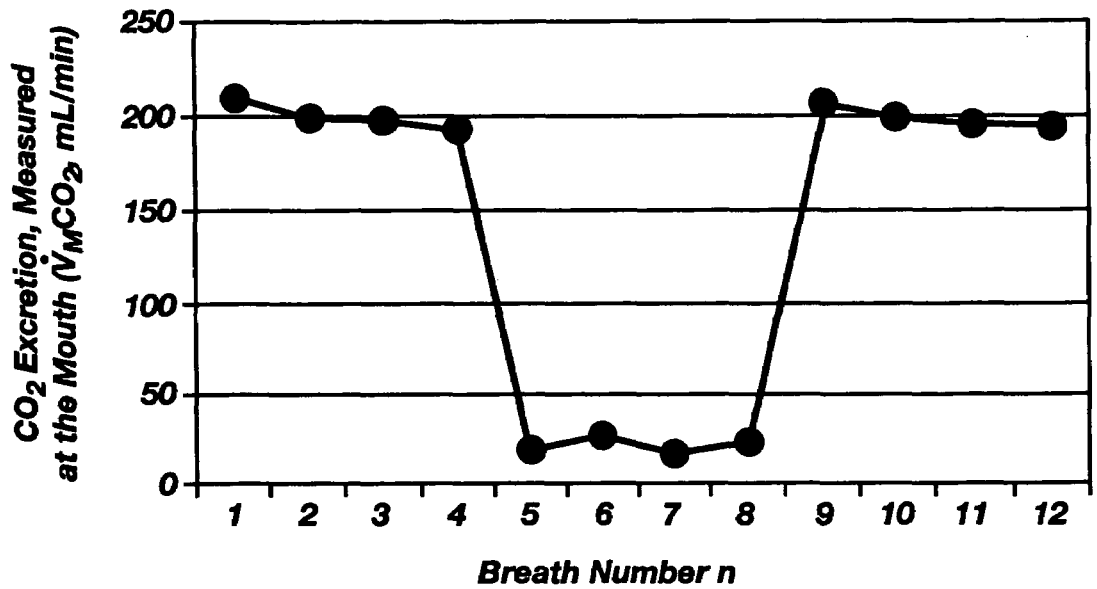
FIG. 2A is a graph depicting $CO_2$ excretion ($\dot{V}_M CO_2$) measurements taken at various breaths by an individual.
Figure 2B:
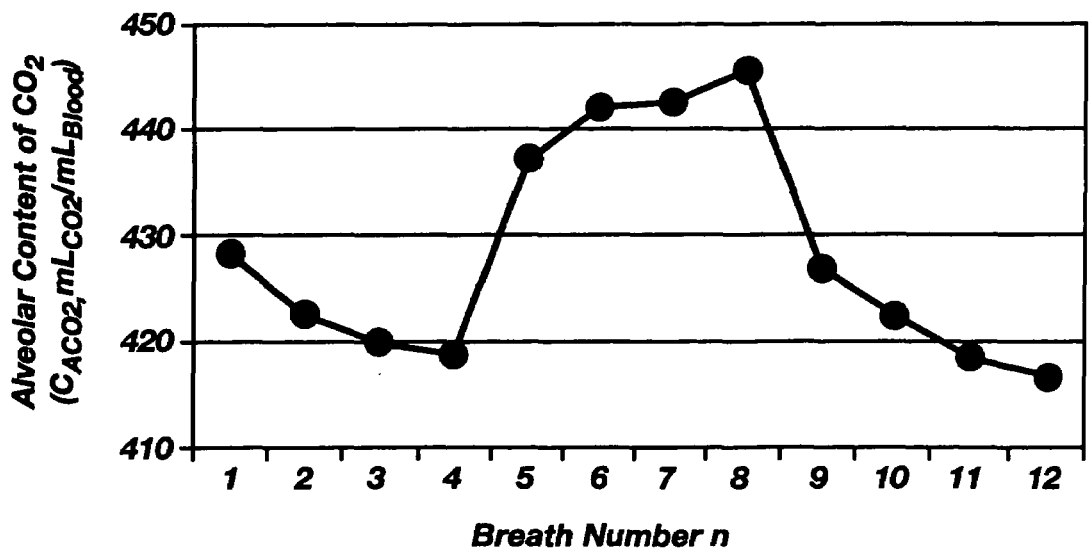
FIG. 2B is a graph depicting measurements of the content of $CO_2$ in the alveolar blood of the individual ($c_{ACO2}$), taken at breaths that correspond to those of the graph of FIG. 2A.
Figure 3:
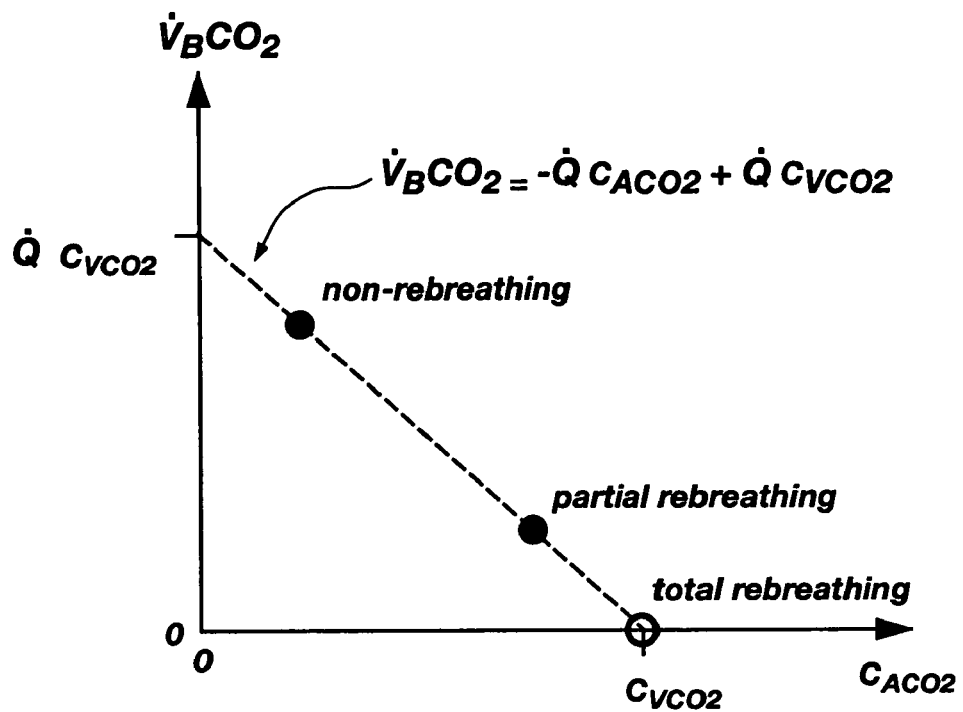
FIG. 3 is a graph in which corresponding $\dot{V}_B CO_2$ and $c_{ACO2}$ measurements are plotted against one another, illustrating all of the plotted points being located in an ideal, substantially in-line relation to one another.
Figure 4:
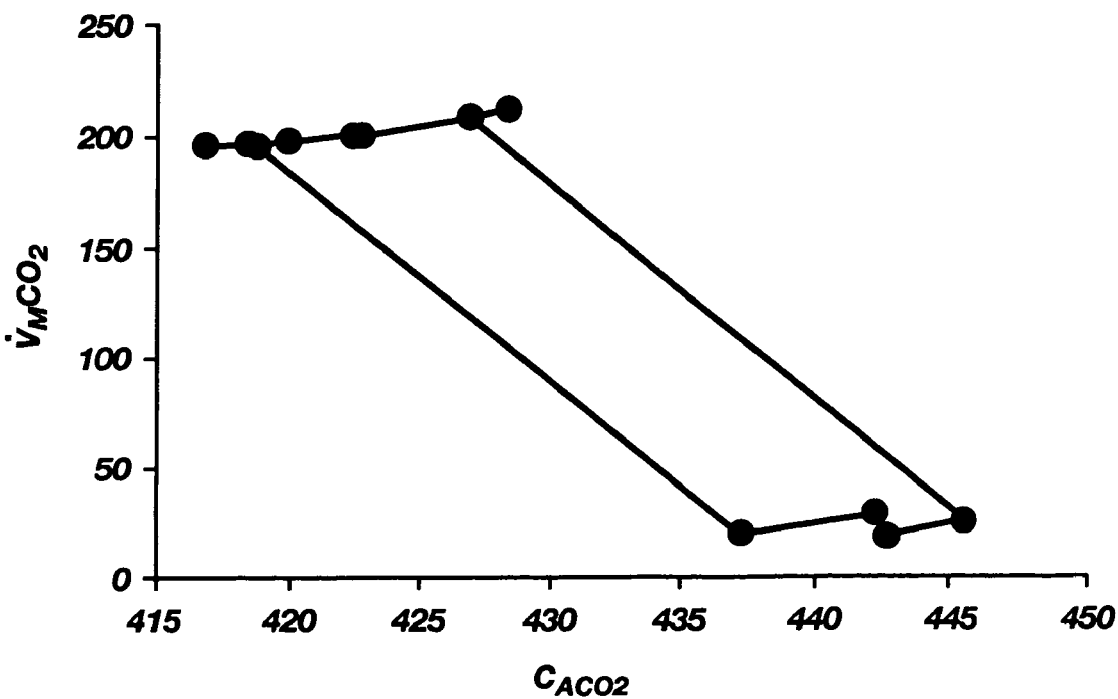
FIG. 4 is a graph in which corresponding $\dot{V}_M CO_2$ and $c_{ACO2}$ data from FIGS. 2A and 2B are plotted against one another and are arranged in a so-called "loop;"
Figure 8A:
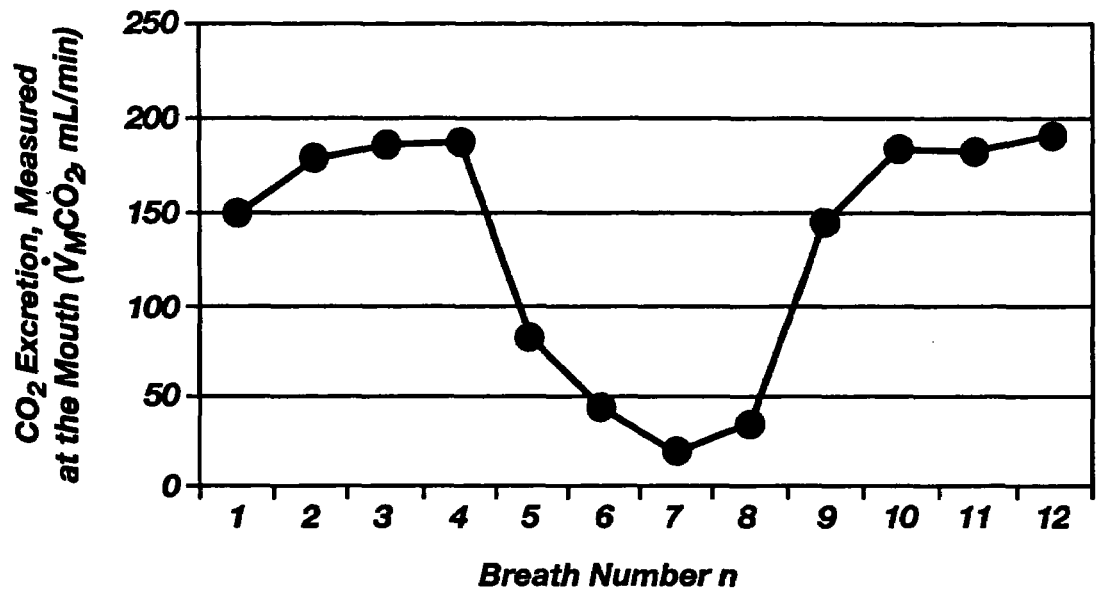
FIG. 8A is a graph depicting $CO_2$ excretion ($\dot{V}_M CO_2$) measurements taken at various breaths by an individual that correspond to the data points depicted in FIG. 2A and which have been transformed, filtered, or otherwise corrected in accordance with teachings of the present invention.
Figure 8B:
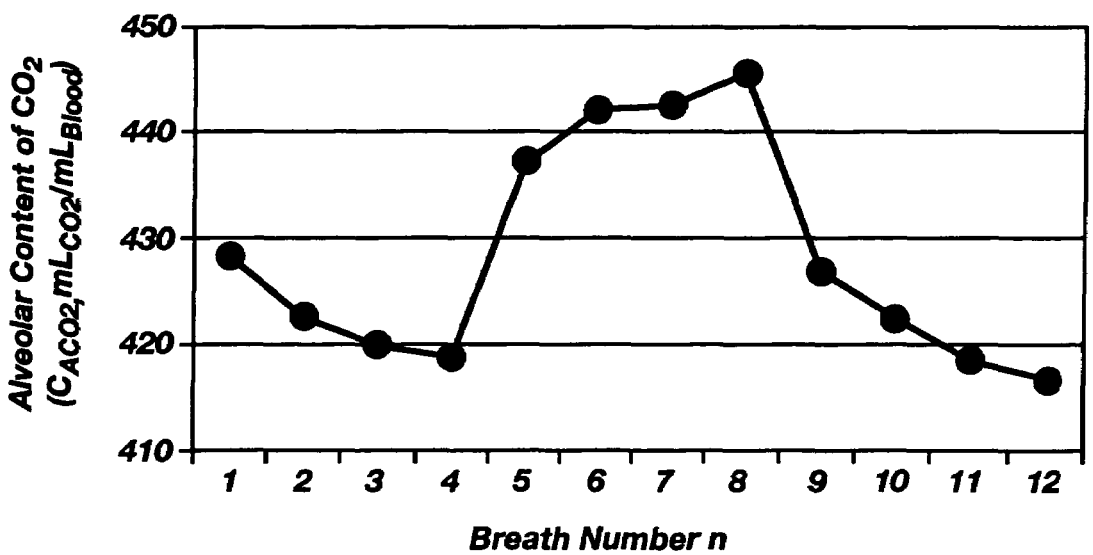
FIG. 8B is a graph depicting measurements of the content of $CO_2$ in the alveolar blood of the individual ($c_{ACO2}$), which correspond to the data points depicted in FIG. 2B and which have been taken at breaths that correspond to those of the graphs of FIGS. 2A and 8A.
Figure 9:
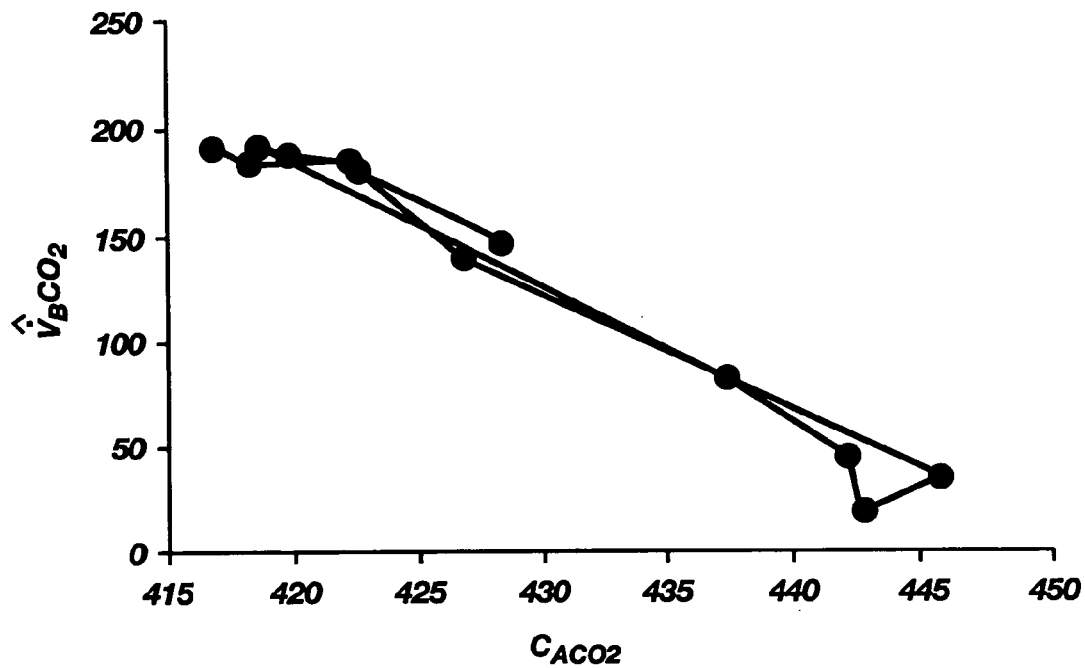
FIG. 9 is a plot of the transformed $\dot{V}_M CO_2$ data points of FIG. 8A against the $c_{ACO2}$ data points of FIG. 8B, in which the plotted points are substantially in-line with one another.

An example of the result of applying the algorithms of equations (15), (16), and (9) to the data shown in FIGS. 2A and 2B is depicted in FIGS. 8A, 8B, and 9. In the $\dot{V}_B CO_2$ and $c_{ACO2}$ trend plots of FIGS. 8A and 8B, respectively, the $\hat{V}_B CO_2$ signal appears to have been "slowed down" to match the corresponding, inverted $c_{ACO2}$ signal. As a result, plotting the $\dot{V}_B CO_2$ signal against the $c_{ACO2}$ signal, the data points fall more closely to the line predicted by the carbon dioxide Fick equation (equation (5) and FIG. 3), as shown in FIG. 9.

Figure 12:
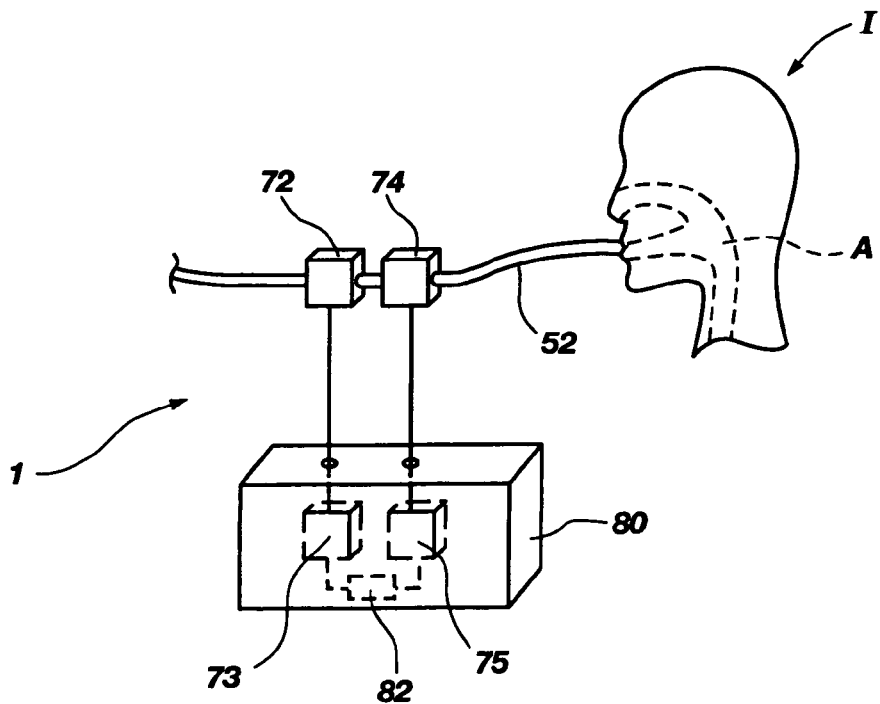
FIG. 12 is a schematic representation of an example of a monitoring system incorporating teachings of the present invention.

Turning now to FIG. 12, a schematic representation of a diagnostic system 1 incorporating teachings of the present invention is illustrated. Diagnostic system 1 includes, among other things, a tubular airway 52 in communication with the airway A of an individual I, as well as a flow meter 72 and a carbon dioxide sensor 74 positioned along tubular airway 52. Flow meter 72 and carbon dioxide sensor 74 communicate signals to corresponding monitors 73 and 75, which communicate electronically with a processor 82 of a respiratory monitor 80. Processor 82 is programmed to determine at least $VCO_2$ and $p_{etCO2}$ based on signals communicated thereto from flow meter 72 and carbon dioxide sensor 74. In addition, processor 82 may be programmed to use signals from one or both of flow meter 72 and carbon dioxide sensor 74 or calculated parameters (e.g., $VCO_2$ and $p_{etCO2}$) in the above-described algorithms to facilitate the substantially noninvasive and accurate determination of pulmonary capillary blood flow or cardiac output of the individual. Alternatively, such calculations may be made manually.

EXAMPLE

Using a common protocol, anesthesia was induced in five mongrel dogs (25.8 kg to 42.4 kg) using tiletamine and zolazepam. Each animal was intubated and mechanically ventilated throughout the experiment. Anesthesia was maintained with halothane and isoflurane. Cardiac output was increased during the experiment using dobutamine and decreased using halothane, xylazine, or a combination thereof.

A DUALTHERM (B. Braun Medical Inc., Bethlehem, Pa.) pulmonary artery catheter was placed and used for periodic thermodilution cardiac output measurements. The DUALTHERM catheter uses a dual thermister that directly measured injectate temperature, thereby eliminating errors caused by faulty injectate temperature measurement. Thermodilution cardiac output measurements, using about 10 ml of iced saline, were taken in triplicate every 10 minutes at random times during the respiratory cycle.

$\dot{V}_M CO_2$ and $p_{etCO2}$ were recorded using a commercially available partial rebreathing system (NICO$_2$®, Novametrix Medical Systems Inc., Wallingford, Conn.). The flow and $CO_2$ sensors used by the rebreathing system were placed in the breathing circuit between the endotracheal tube and the wye piece of the breathing circuit. Partial rebreathing cycles were comprised of a 30 second rebreathing and a 30 second recovery period. Rebreathing cycles were run continuously every 60 seconds throughout the experiments.

Respiratory data from the NICO$_2$® monitor were automatically recorded on a personal computer for later analysis. The stored respiratory data was processed using the model-based lung stores compensation method described above, using equations (12) and (5). The resulting partial rebreathing cardiac output measurements were compared against simultaneously collected thermodilution cardiac output measurements.

Figure 10:
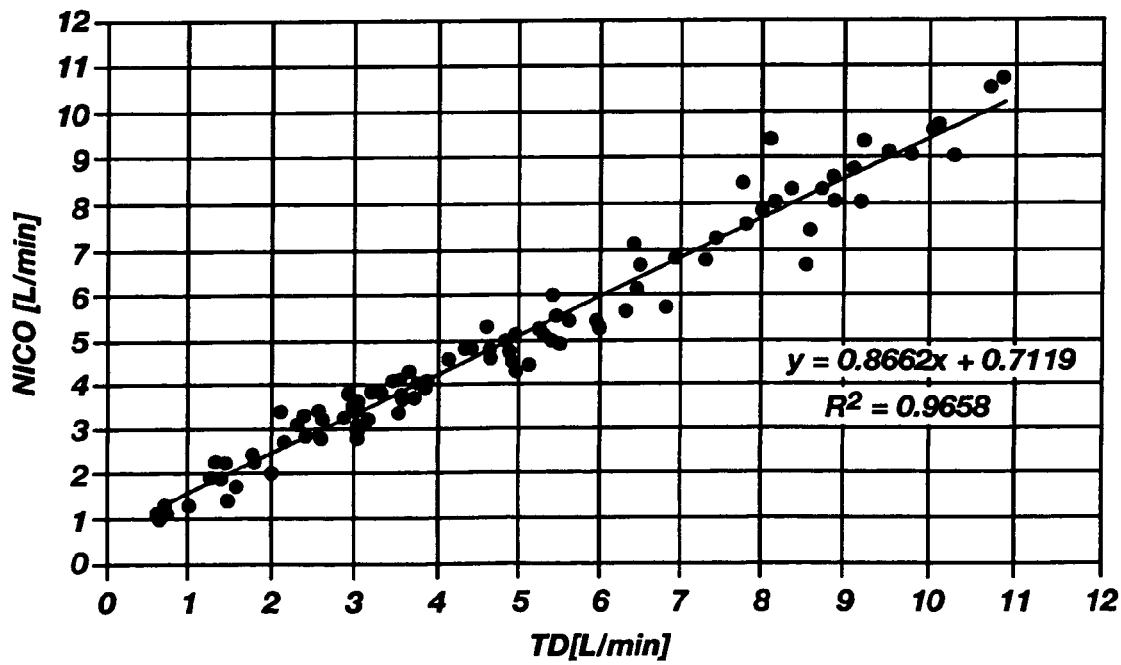
FIG. 10 is a graph in which noninvasively obtained flow data that were determined in accordance with teachings of the present invention are compared with corresponding flow data obtained by highly accurate, invasive thermodilution techniques, which graph illustrates the high correlation between pulmonary capillary blood flow or cardiac output measurements obtained by methods that incorporate teachings of the present invention and those obtained by use of thermodilution techniques.
Figure 11:
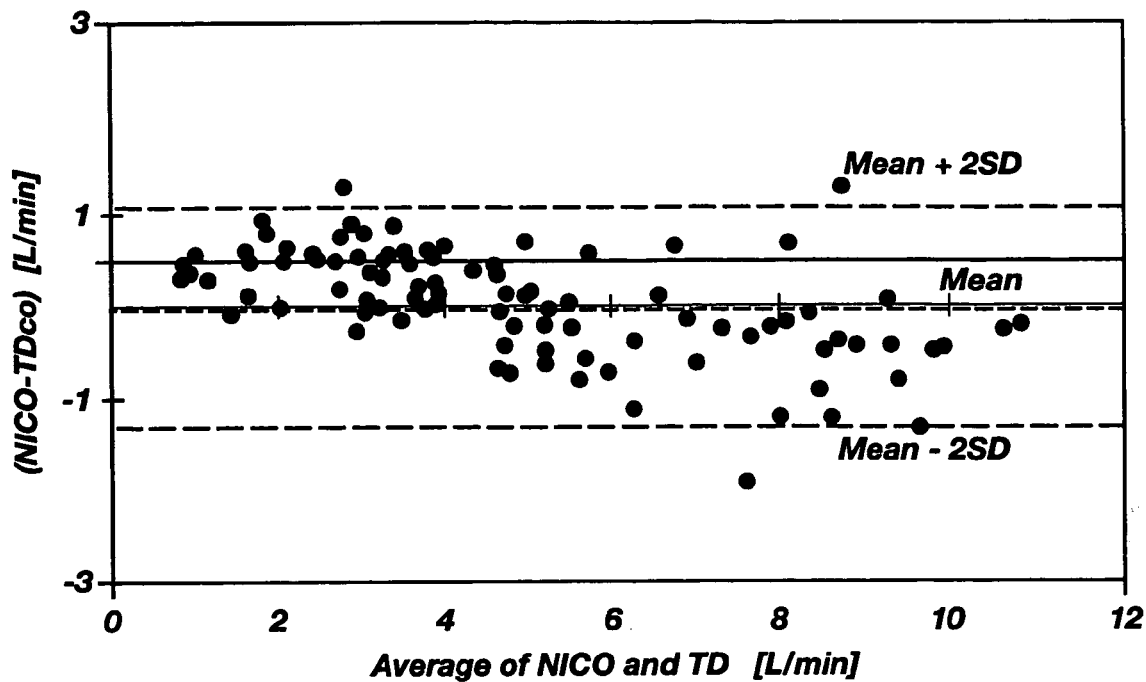
FIG. 11 illustrates the differences between corresponding flow measurements obtained by methods of the present invention and those obtained by thermodilution techniques.

A total of 96 thermodilution cardiac output measurements, ranging from 0.64 to 10.88 L/min, were taken. Regression analysis of the paired partial rebreathing and thermodilution measurements, shown in the graph of FIG. 10, gave a correlation coefficient ($r^2$) of 0.966. As depicted in FIG. 11, Bland-Altman analysis showed a bias of −0.059 L/min and a standard deviation of 0.58 L/min (±24% according to Critchley, LAH, et al., A meta-analysis of studies using bias and precision statistics to compare cardiac output measurement techniques, J. CLIN. MONITORING 15: 85–91 (1999)). The 95% confidence interval of the difference between rebreathing cardiac output and thermodilution cardiac output was between −1.19 and 1.08 L/min.

These comparisons evidence the accuracy with which pulmonary capillary blood flow and cardiac output measurements may be obtained when teachings of the present invention are employed.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A method for optimizing the accuracy of at least one of a carbon dioxide elimination measurement obtained from a subject based on carbon dioxide stores of a respiratory tract of the subject, comprising applying a filter comprising an algorithm that employs a transformation coefficient based on carbon dioxide stores to a carbon dioxide elimination measurement of at least one breath by the subject and a carbon dioxide excretion estimate or carbon dioxide excretion signal for at least another breath.

2. The method of claim 1, wherein applying comprises applying a filter comprising an algorithm that employs a transformation coefficient based on a functional residual capacity of the subject.

3. The method of claim 1, wherein applying comprises applying a filter comprising an algorithm that employs a transformation coefficient based on a functional residual capacity of the subject and an amount of carbon dioxide that has diffused into lung tissues.

4. The method of claim 1, wherein applying comprises applying a low-pass filter.

5. The method of claim 4, wherein applying the low-pass filter comprises employing the following formula:

$$(1-\alpha)\dot{V}_M CO_2(n) + \alpha \dot{V}_B CO_2(n-1),$$

where $\dot{V}_M CO_2(n)$ is the carbon dioxide elimination measurement, $\dot{V}_B CO_2(n-1)$ is an estimate of carbon dioxide excretion of another breath, and $\alpha$ is the transformation coefficient based on an estimate of the carbon dioxide stores of the respiratory tract of the subject.

6. The method of claim 1, further comprising:
estimating carbon dioxide excretion for the at least another breath.

7. The method of claim 6, wherein estimating carbon dioxide excretion for the at least another breath includes accounting for carbon dioxide stores in the respiratory tract of the subject during the at least another breath.

8. The method of claim 7, wherein accounting for carbon dioxide stores comprises accounting for functional residual capacity during the at least another breath.

9. The method of claim 7, wherein accounting for carbon dioxide stores comprises accounting for functional residual capacity and carbon dioxide within tissues of the respiratory tract during the at least another breath.

10. The method of claim 6, wherein estimating carbon dioxide excretion of the at least another breath includes employing the formula:

$$\dot{V}_M CO_2(n) + \hat{V}_A^*(n)[f_A CO_2(n) - f_A CO_2(n-1)]RR,$$

where $\dot{V}_M CO_2(n)$ is the carbon dioxide elimination measurement for the at least another breath, $\hat{V}_A^*(n)$ is an estimate of a volume of the carbon dioxide stores of the respiratory tract of the subject during the at least another breath, $[f_A CO_2(n) - f_A CO_2(n-1)]$ is a difference between a fraction of carbon dioxide in alveoli of the respiratory tract of the subject for the at least another breath and an immediately preceding breath, and RR is a respiratory rate of the subject.

11. The method of claim 1, further comprising determining an optimal value for the transformation coefficient.

12. The method of claim 11, wherein determining the optimal value comprises at least one of iterative searching, rote searching, gradient searching, use of a set of predetermined equations, and adaptive filtering.

13. The method of claim 11, further comprising, following the act of applying the filter, adjusting the estimate of carbon dioxide excretion of the at least another breath to improve a correlation between the carbon dioxide elimination measurement and an indicator of the content of carbon dioxide in blood of the subject.

14. A method for improving an accuracy of a respiratory signal, comprising:
obtaining the respiratory signal from respiration of a subject during at least two breaths; and
applying a filter comprising an algorithm that employs a transformation coefficient based on carbon dioxide stores of a respiratory tract of the subject to the respiratory signal and measured or estimated respiratory data from another breath.

15. The method of claim 14, wherein applying the filter comprises applying a filter comprising an algorithm that employs a transformation coefficient based on functional residual capacity of the respiratory tract.

16. The method of claim 14, wherein applying the filter comprises applying a filter comprising an algorithm that employs a transformation coefficient based on functional residual capacity of the respiratory tract and carbon dioxide in tissues of the respiratory tract.

17. The method of claim 14, wherein applying the filter comprises employing an estimate of at least one of a volume of the carbon dioxide stores of the respiratory tract of the subject and a flow of carbon dioxide into or out of the carbon dioxide stores.

18. The method of claim 14, wherein obtaining the respiratory signal comprises obtaining a carbon dioxide elimination signal from respiration of the subject.

19. The method of claim 18, wherein applying the filter comprises employing the carbon dioxide elimination signal in the following algorithm:

$$(1-\alpha)\dot{V}_M CO_2(n) + \alpha \dot{V}_B CO_2(n-1),$$

where $\dot{V}_M CO_2(n)$ is the carbon dioxide elimination signal, $\dot{V}_B CO_2(n-1)$ is carbon dioxide excretion and comprises at least a part of the measured or estimated respiratory data from the another breath, and $\alpha$ is the transformation coefficient.

20. The method of claim 18, further comprising:
estimating carbon dioxide excretion for the another breath.

21. The method of claim 20, wherein estimating carbon dioxide excretion for the another breath includes accounting for carbon dioxide stores in the respiratory tract of the subject during the another breath.

22. The method of claim 21, wherein accounting for carbon dioxide stores comprises accounting for functional residual capacity during the another breath.

23. The method of claim 21, wherein accounting for carbon dioxide stores comprises accounting for functional residual capacity and carbon dioxide within tissues of the respiratory tract during the another breath.

24. The method of claim 20, wherein estimating carbon dioxide excretion of the another breath includes employing the formula:

$$\dot{V}_M CO_2(n) + \hat{V}_A^*(n)[f_A CO_2(n) - f_A CO_2(n-1)]RR,$$

where $\dot{V}_M CO_2(n)$ is the carbon dioxide elimination measurement for the another breath, $\hat{V}_A^*(n)$ is an estimate of a volume of the carbon dioxide stores of the respiratory tract of the subject during the another breath, $[f_A CO_2(n) - f_A CO_2(n-1)]$ is a difference between a fraction of carbon dioxide in alveoli of the respiratory tract of the subject for the another breath and an immediately preceding breath, and RR is a respiratory rate of the subject.

25. The method of claim 14, further comprising determining an optimal value for the transformation coefficient.

26. The method of claim 25, wherein determining the optimal value comprises at least one of iterative searching, rote searching, gradient searching, use of a set of predetermined equations, and adaptive filtering.

27. The method of claim 25, further comprising, following the act of applying the filter, adjusting the estimate of carbon dioxide excretion of the at least another breath to improve a correlation between the carbon dioxide elimination measurement and an indicator of the content of carbon dioxide in blood of the subject.

28. A respiratory monitoring device configured to optimize the accuracy of a respiratory signal obtained from at least one breath by a subject by accounting for carbon dioxide stores of a respiratory tract of the subject, comprising:
    at least one processing element programmed to apply a filter comprising an algorithm that employs a transformation coefficient based on carbon dioxide stores of a respiratory tract of the subject to the respiratory signal and measured or estimated respiratory data from another breath.

29. The respiratory monitoring device of claim 28, wherein the at least one processing element is programmed to apply a filter comprising an algorithm that employs a transformation coefficient based on functional residual capacity of the respiratory tract.

30. The respiratory monitoring device of claim 28, wherein the at least one processing element is programmed to apply a filter comprising an algorithm that employs a transformation coefficient based on functional residual capacity of the respiratory tract and carbon dioxide in tissues of the respiratory tract.

31. The respiratory monitoring device of claim 28, wherein the at least one processing element is programmed to apply a filter comprising an algorithm that comprises an estimate of at least one of a volume of the carbon dioxide stores of the respiratory tract of the subject and a flow of carbon dioxide into or out of the carbon dioxide stores.

32. The respiratory monitoring device of claim 28, further comprising:

at least one sensor for obtaining the respiratory signal.

33. The respiratory monitoring device of claim 32, wherein the at least one sensor is used to obtain a carbon dioxide elimination signal from respiration of the subject.

34. The respiratory monitoring device of claim 33, wherein the at least one processing element is programmed to apply the following algorithm to the carbon dioxide elimination signal:

$$(1-\alpha)\dot{V}_M CO_2(n) + \alpha \dot{V}_B CO_2(n-1),$$

where $\dot{V}_M CO_2(n)$ is the carbon dioxide elimination signal, $\dot{V}_B CO_2(n-1)$ is carbon dioxide excretion and comprises at least a part of the measured or estimated respiratory data from the another breath, and $\alpha$ is the transformation coefficient.

35. The respiratory monitoring device of claim 33, wherein the at least one processing element is also programmed to estimate carbon dioxide excretion for the another breath.

36. The respiratory monitoring device of claim 35, wherein, in estimating carbon dioxide excretion for the another breath, the at least one processing element is programmed to account for carbon dioxide stores in the respiratory tract of the subject during the another breath.

37. The respiratory monitoring device of claim 36, wherein the at least one processing element is programmed to account for carbon dioxide stores comprising functional residual capacity during the another breath.

38. The respiratory monitoring device of claim 37, wherein the at least one processing element is programmed to account for carbon dioxide stores further comprising carbon dioxide within tissues of the respiratory tract during the another breath.

39. The respiratory monitoring device of claim 35, wherein the at least one processing element is programmed to apply formula to the carbon dioxide elimination measurement for the another breath:

$$\dot{V}_M CO_2(n) + \hat{V}_A^*(n)[f_A CO_2(n) - f_A CO_2(n-1)]RR,$$

where $\dot{V}_M CO_2(n)$ is the carbon dioxide elimination measurement for the another breath, $\hat{V}_A^*(n)$ is an estimate of a volume of the carbon dioxide stores of the respiratory tract of the subject during the another breath, $[f_A CO_2(n) - f_A CO_2(n-1)]$ is a difference between a fraction of carbon dioxide in alveoli of the respiratory tract of the subject for the another breath and an immediately preceding breath, and RR is a respiratory rate of the subject.

40. The respiratory monitoring device of claim 28, wherein the at least one processing element is programmed to determine an optimal value for the transformation coefficient.

41. The respiratory monitoring device of claim 40, wherein the at least one processing element is programmed to conduct at least one of an iterative search, a rote search, a gradient search, a set of predetermined equations, and adaptive filtering to determine the optimal value.

42. The respiratory monitoring device of claim 40, wherein the at least one processing element is programmed to adjust the estimate of carbon dioxide excretion of the at least another breath to improve a correlation between the carbon dioxide elimination measurement and an indicator of the content of carbon dioxide in blood of the subject following application of the filter.

* * * * *